United States Patent [19]

Tucker et al.

[11] 4,377,949

[45] Mar. 29, 1983

[54] MOBILE SAMPLER FOR USE IN ACQUIRING SAMPLES OF TERRESTIAL ATMOSPHERIC GASES

[76] Inventors: Alan M. Lovelace, Administrator of the National Aeronautics and Space Administration, with respect to an invention of Curtis E. Tucker, Pasadena; Harold P. Holway, Las Crescenta, both of Calif.

[21] Appl. No.: 246,777

[22] Filed: Mar. 23, 1981

[51] Int. Cl.$^3$ .............................................. G01N 1/24
[52] U.S. Cl. .............................. 73/863.31; 73/863.83; 73/864.63; 220/335
[58] Field of Search ............ 73/863.31, 864.63, 863.23, 73/864.73, 863.81, 863.83, 863.58, 863.61; 220/335, 345

[56] References Cited

U.S. PATENT DOCUMENTS

| | | | |
|---|---|---|---|
| 3,339,417 | 9/1967 | Richard | 73/864.63 |
| 3,489,012 | 1/1970 | Niskin | 73/863.31 |
| 3,531,995 | 10/1970 | Barker | 73/864.62 |
| 3,731,539 | 5/1973 | Brittan et al. | 73/863.31 |
| 3,884,081 | 5/1975 | Griffith | 73/863.31 |
| 3,921,456 | 11/1975 | Newcomb, Jr. et al. | 73/863.31 |

*Primary Examiner*—Steven L. Stephan

*Attorney, Agent, or Firm*—Thomas H. Jones; John R. Manning

[57] ABSTRACT

A mobile sampler 10 for use in acquiring samples of terrestial atmospheric gasses from a free body of such gasses. The device is chracterized by a plurality of tubular bodies 12 adapted to be mounted in side-by-side relation on a motorized highway vehicle V in mutual parallelism with the axis of the normal path of travel for the vehicle; each of the bodies is of a cylindrical configuration and has an axial opening disposed at each of its opposite ends whereby a linear flow path is defined therethrough, a pair of pivotally supported, spring-biased sealing caps 14A and 14B mounted adjacent the ends of the body and continuously urged into hermetic sealing relationship therewith, a restraint for securing the caps against spring-urged pivotal displacement, including a separable, normally tensioned line 52 interconnecting the caps and an operable release mechanism for simultaneously releasing the caps for spring-urged displacement, including a hot wire cutter 54 for separating said line, whereby samples of air are trapped in the body as the caps are spring-driven to assume an hermetically sealed relation with the openings defined in each of the opposite ends of the body.

5 Claims, 5 Drawing Figures

MOBILE SAMPLER FOR USE IN ACQUIRING SAMPLES OF TERRESTIAL ATMOSPHERIC GASES

ORIGIN OF THE INVENTION

The invention described herein was made in the performance of work under a NASA Contract and is subject to the provisions of Section 305 of the National Aeronautics and Space Act of 1958, Public Law 85–568 (72 STAT, 435; 42 U.S.C. 2457).

BACKGROUND OF THE INVENTION

1. Field of the Invention

The instant invention generally relates to an air sampler suitable for use in obtaining tracer samples "on the fly" on highways, in tunnels, and the like, for analysis and similar purposes.

2. Description of the Prior Art

Heretofore it has been common practice to obtain air or tracer samples employing "fixed-site" samplers which often require specific governmental or official approval.

It is the general purpose of the instant invention to provide an air sampler particularly suited for use with test transport vehicles in an acquisition of tracer samples of terrestial atmospheric gasses from free bodies of atmospheric gasses encountered at random locations such as along highways, in tunnels, and the like.

OBJECTS AND SUMMARY OF THE INVENTION

It is an object of the instant invention to provide an improved method for capturing tracer samples of terrestial atmospheric gasses.

It is another object to provide an improved device for capturing tracer samples of terrestial atmospheric gasses.

It is another object to provide a mobile sampler for use in acquiring samples of terrestial atmospheric gasses from free bodies of such gasses, as may be found along highways, tunnels, and the like and transporting the acquired samples to remote facilities and thereafter accommodate a forced discharge of the samples preparatory to an analysis thereof.

These and other objects and advantages are achieved through the use of a device characterized by a plurality of tubular bodies, each being of a substantially cylindrical, open-end configuration, and a pair of spring-loaded caps for simultaneously sealing the opposite ends of the body, a restraint mechanism for simultaneously releasing the caps, and a discharge plunger and nipple for facilitating expulsion of the samples, as will become more readily apparent by reference to the following description and claims in light of the accompanying drawings.

DESCRIPTION OF THE PREFERRED EMBODIMENT

Figure 2:
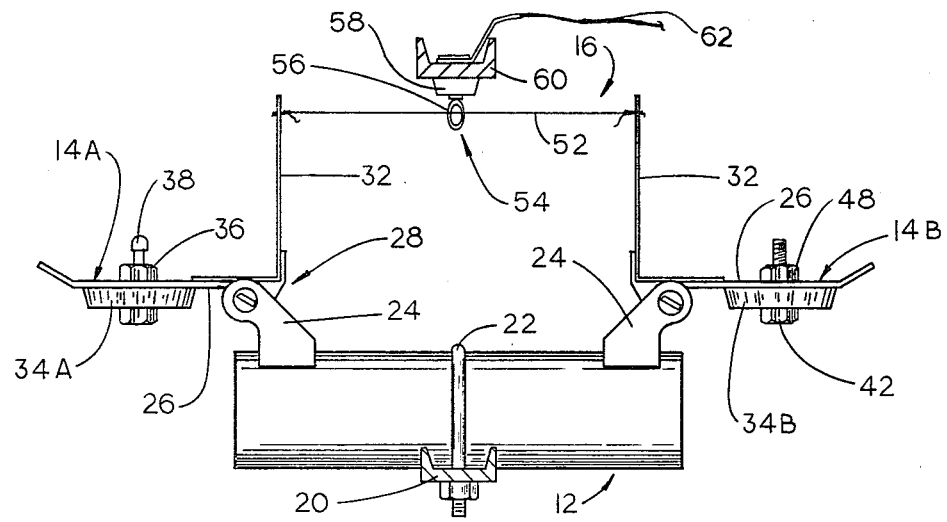
FIG. 2 is a sectional view taken generally along lines 2—2 of FIG. 1, depicting an open condition for one of a plurality of bodies included in the mobile air sampler shown in FIG. 1.

Referring now to the drawings, with more particularity, wherein like reference characters designate like or corresponding parts throughout the several views, there is shown a device, generally designated 10, embodying the principles of the instant invention. As shown, the device 10 includes a plurality of similar open-end bodies 12. Since the bodies 12 are of a substantially common design, a detailed description of a single one of the bodies is deemed adequate to provide for a complete understanding of the invention. Each of the bodies is adapted to be hermetically sealed by a pair of caps 14A and 14B, FIG. 2, normally supported in a body-opening disposition, relative to the open ends of the body, by a restraint mechanism, generally designated 16, FIG. 2.

Figure 1:
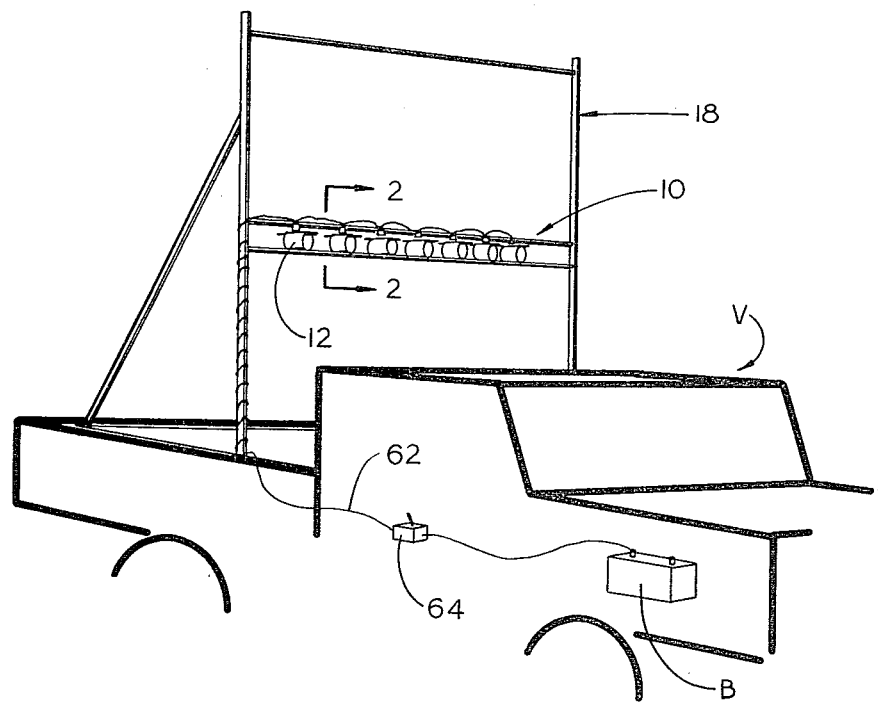
FIG. 1 is a perspective view of a mobile air sampler depicted in an operational environment.

As shown in FIG. 1, the device 10 is mounted aboard a highway vehicle, generally designated V, by means of superstructure 18, of suitable design. The particular superstructure employed in mounting the device 10 aboard the vehicle is varied as desired and may include supporting structure capable of mounting the bodies 12 in any grouping desired. Consequently, a detailed description of the superstructure 18 is omitted in the interest of brevity. It suffices to understand, however, that the superstructure 18 serves to support the bodies 12 in a manner such that the longitudinal axes of the bodies are arranged in substantial parallelism with the axis of the intended path of travel for the vehicle V and in the airstream established thereover as the vehicle travels said path.

Turning again for a moment to FIG. 2, it is noted that each of the bodies 12 is supported by a transverse base 20 to which it is affixed by a suitable fastener, such as a conventional U-bolt 22, of conventional design. Here again, the device employed in mounting the bodies is deemed to be a matter of convenience only and is varied as desired.

Each of the bodies 12 is of a cylindrical configuration through which freely passes a stream of air as the vehicle experiences locomotion. Consequently, so long as the caps 14A and 14B are supported in a tube-opened disposition, the stream of air is passed therethrough with minimal impedance, however, once the caps 14A and 14B are seated in hermetically sealed relation with the opposite ends of the body 12, a sample of ambient atmospheric gasses is trapped within the body.

It is important to note that each of the caps 14A and 14B is supported by a pivotal mount 24. These are welded or otherwise rigidly affixed to the body 12, adjacent the ends thereof. In practice, each of the caps includes a planar base plate 26 supported by a suitable angulated hinge plate 28 coupled with the mount 24 through a hinge pin 29. As a practical matter, the plate 28 is shown as an integral extension of the plate 26, although it need not be so formed. A torsional spring 30 is concentrically related to the pin 29 and connected to the plate 28 for continuously urging the base plate 26 in pivotal displacement, in a direction such that the caps 14A and 14B are continuously urged toward an hermetically sealed relation with the open ends of the body 12.

Figure 3:
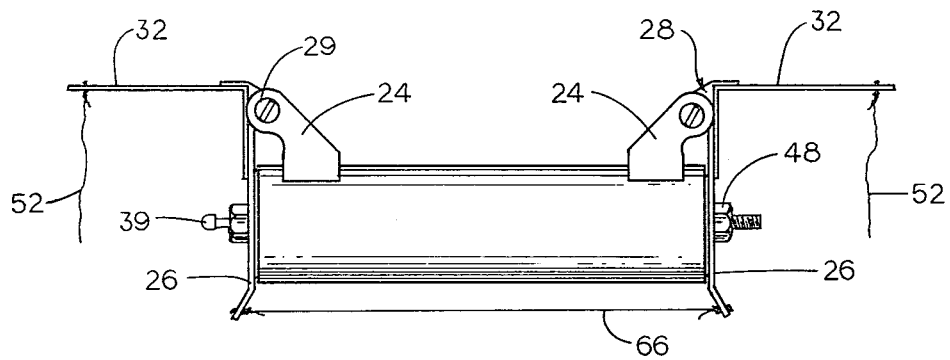
FIG. 3 is a vertically sectioned view depicting a sealed condition for the body of FIG. 2.
Figure 4:
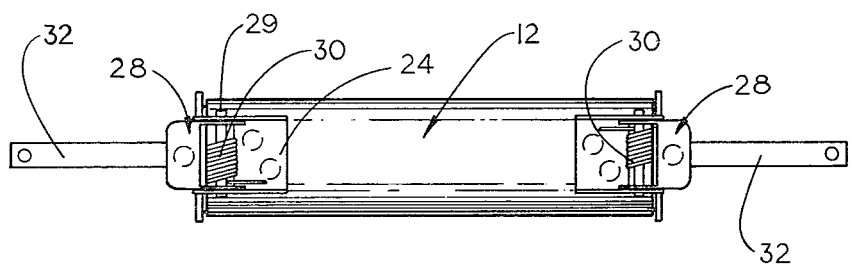
FIG. 4 is a top plan view of the sealed body shown in FIG. 3.

It is here also important to note that mounted on and projected from the hinge plate 28, for each of the caps 14A and 14B, there is an angulated arm 32. This arm, as shown, is fastened to the base plate 26, as well as to the hinge plate 28, and projects normally therefrom. The arms 32 are fastened to the plates in a suitable manner, such as by spot welding or the like. It also is important to note that the arms 32 are arranged in paired relation. Moreover, when the caps 14A and 14B are in a tube-open disposition, the arms 32 are normally related to the planes of the openings formed in the body, whereby the arms of each pair of arms 32 are projected in parallelism. The arms 32 are supported in parallelism by the restraint mechanism 16, so long as the plates 26 are disposed in a body-open disposition in mutual coplanar alignment. However, once the restraint mechanism is rendered ineffective, the torsion springs 30, for the caps 14A and 14B, initiate pivotal displacement of the base plates 26, about the axes of the pins 29, for thus causing the base plates 26 to assume a body-closed disposition, transversely of the axis of the body 12, a position in which the arms 32 of the pair extend in parallelism with the axis of the body, as best illustrated in FIG. 3.

As a practical matter, there is mounted on each of the base plates 26, for the caps 14A and 14B, resilient pads 34A and 34B, FIGS. 2 and 5, hereinafter referred to as sealing plugs. As best illustrated in FIG. 2, the plugs 34A and 34B are of a tapered, or truncated, conical configuration and, preferably, are formed of a resilient material, such as rubber, which accommodates the establishment of an hermetic seal being formed as the caps 14A and 14B are caused to assume a body-closed disposition, relative to the openings formed in ends of the body 12. It is also imperative that the plug 34B be suitably sized or dimensioned as to accommodate its passage axially through the body 12, while maintaining an hermetically sealed relationship with the internal surface thereof, for reasons hereinafter more fully set forth.

Figure 5:
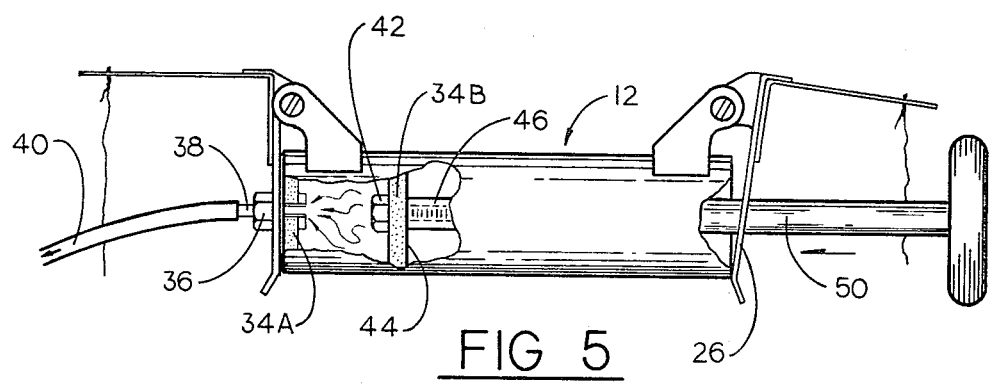
FIG. 5 is a fragmented, cross-sectional view depicting an operational discharge of a tracer sample acquired by the mobile air sampler shown in FIG. 1.

As best illustrated in FIGS. 2 and 5, the sealing plug 34A is connected to the base plate 26, of the cap 14A by means of a fitting 36 for a nipple projected axially through the plug 34A and the plate 26 associated therewith. The nipple 38, normally closed by a cap 39, accommodates a coupling of a tubular conduit 40 in communicating relation with the interior of the body 12 once the body is closed by the cap 14A. Similarly, the sealing plug 34B is mounted on the plate 26 for the cap 14B by a mandrel 42 extended axially through the plug 34B and the base plate 26. The plug 34B is supported in place by a headed mandrel 42 and a base plate 44, FIG. 5. In practice, the mandrel 42 consists of a screw-threaded shaft 46, FIG. 5, projected from the head thereof through the plug 34B and a concentric opening, not designated, formed in the plate 26, to receive a nut 48, suitable for securing the mandrel, and consequently the plug 34B, in coupled relation with the plate 46. As best illustrated in FIG. 5, once the nut 48 is removed, a shaft forming a push-rod 50 may be coupled therewith in a screw-threaded fashion, for thus uniting the plug 34B with the push-rod 50. The diameter of the push-rod 50 is, of course, such that passage thereof through the concentric opening formed in the plate 26 for the cap 14B readily is facilitated. When the plug 34B thus is adapted to be coupled with the push-rod 50, so as to function as a piston head in response to axial forces applied inwardly to the push-rod 50 for separating the plug from the plate.

Turning again to FIG. 2, it can be seen that the restraint mechanism 16 includes a tension line 52, formed of a suitable, heat responsive material, including nylon or the like. The line 52 is coupled at its opposite ends to the projected ends of the arms 32 for the caps 14A and 14B and, consequently, is tensioned by the springs 30 acting on the caps 14A and 14B.

In order to release the caps 14A and 14B for pivotal displacement, under the influence of the torsion springs 30, aforementioned, a hot wire cutter 54 is provided in close proximity with the line 52. The cutter 54, as shown, includes a hot wire loop 56 of an annular configuration. For the sake of simplicity, the hot wire loop is depicted as an annulus having an opening through which passes the line 52. The hot wire loop 56 preferably comprises a resistance hearing element of suitable design, supported by a junction box 58 which is, in turn, suspended from a transverse member 60. The loop 56 is electrically connected with a battery B, FIG. 1, via a suitable electrical lead 62, having a normally open toggle switch 64 interposed therein. The switch 64 is employed to complete a circuit between the battery B and the hot wire loop upon a closing thereof. Of course, upon a closing of the switch 64, an electrical current is caused to pass through the hot wire loop 56 for thus causing it to heat to a temperature sufficient to melt or otherwise "burn" the line 52 sufficiently for accommodating a separation while under the tension of the torsion springs 30. Thus, the caps 14A and 14B are simultaneously released for simultaneous displacement into an hermetically sealed relation with the openings located at the opposite end of the body 12. While the sampler, as shown, is adapted to effect a simultaneous release of all of the caps, it is well within the scope of the invention to accommodate a release of the caps for the bodies 12 independently or sequentially, as desired.

OPERATION

It is believed that in view of the foregoing description, the operation of the instant invention will be understood completely. However, in the interest of assuring that an understanding of the invention hereinbefore described is provided for, the operation of the invention will, at this point, briefly be reviewed.

With the device 10 mounted on the superstructure 18 in a manner such that the bodies 12 are arranged in mutual parallelism with the axis of the intended direction of travel for the vehicle V, the device may be readied for operation. Initially, the caps 14A and 14B are pivotally displaced into co-planar relation and supported in such dispositions by the line 52 secured to the ends of the arms 32 projected in mutual parallelism from the base plates 26 for the caps 14A and 14B, FIG. 2. As the vehicle V is caused to progress along a highway, or similar path of travel, a stream of ambient atmospheric gasses is caused to pass axially through the cylindrical bodies 12. At a moment selected by an operator thereof, the switch 64 is closed for causing an electrical current to pass through the heating element of the cutter 54 for thus causing the hot wire loop 56 to heat and thus initiate separation of the line 52. Upon the line 52 being separated, the torsion springs 30 serve to impart pivotal displacement, simultaneously, to the caps 14A and 14B, for thus causing the caps to advance into an hermetically sealed relation with the openings defined in the opposite ends of the bodies 12. Thus the bodies may be said to "snap shut" for entrapping a sample of the gasses. Where desired, the caps 14A and 14B are secured in their closed condition by means of a suitable line 66, FIG. 3, extended between the plates 26 for the caps and secured as by tieing or the like. Thus the contents of the bodies 12 comprise tracer samples of the atmospheric gasses caused to flow therethrough prior to the closure of the bodies.

The device 10 subsequently is "torn-down" and the bodies 12 transported to a suitable laboratory, at which point the cap 39 is removed and the conduit 40 attached thereto. At this time, the nut 48 also is removed from the mandrel 42 and the push-rod 50 threadably coupled to the mandrel, whereby the plug 34B thus is connected from a sealing plug and adapted to function as a piston head. The piston head now is axially displaced through the body 12 in response to forces axially inwardly applied to the push-rod 50, as illustrated in FIG. 5. Of course, in response to an axial displacement of the plug 34B, now adapted to function as a piston head, axially through the body 12 the tracer sample of gasses previously trapped within the body is discharged through the nipple 38 and conduit 40 to a suitable device, not shown.

In view of the foregoing, it is believed to be readily apparent that the device of the instant invention provides a practical solution to many of the problems heretofore encountered in providing for a rapid, economic and practical sampling of atmospheric air along highways, in tunnels and the like.

What is claimed is:

1. In a method for capturing tracer samples of atmospheric gasses, the steps comprising:
    establishing a stream of atmospheric gasses axially through a container having an opening at each of its opposite ends;
    closing the container by simultaneously positioning a plug in each of the opposite ends of the container in an hermetically sealed relationship therewith for thereby hermetically sealing within the container an entrapped sample of atmospheric gasses; and
    attaching a gas-extraction conduit to one plug in communicating relation with the interior of the container, and thereafter displacing the plug at the other end of the container along a path extended axially through the container, thereby discharging the entrapped sample of atmospheric gasses from the container through said gas-extraction conduit.

2. A mobile air sampler for use in acquiring tracer samples from a free body of atmospheric gasses, comprising:
    a cylindrical body having an axial opening disposed at each of its opposite ends and a linear flow path for gasses extended therebetween,
    a pair of pivotal, spring-biased sealing caps, each being mounted adjacent one of said openings and continuously urged into an hermetic sealing relationship therewith, each of said caps being spring-biased by a torsion spring connected thereto for urging the cap in pivotal displacement, and each of said caps including a base member having a tapered plug affixed to one face thereof adapted to seat within one of said openings,
    restraint means for securing said caps away from said openings against said spring-urged pivotal displacement including a separable, tensioned line interconnecting said caps, said restraint means including an arm projected normally with respect to said base member to which one end of said line is attached when said caps are secured against pivotal displacement, whereby said line is tensioned, and operable release means for initiating a separation of said line for thereby releasing said caps for simultaneous spring-urged pivotal displacement, said release means comprising a remotely controlled, electrically energizable hot wire cutter disposed adjacent to the midportion of said line and adapted to cut said line upon being heated.

3. An air sampler as defined in claim 2 further comprising a mandrel affixed to one plug and a nipple affixed to the other plug for said pair of caps, and wherein said one plug is removably mounted on the base member associated therewith and sized to accommodate a passage thereof along said flow path in response to force applied thereto through said mandrel.

4. A mobile sampler for use in acquiring samples of terrestial atmospheric gasses comprising:
    A. a plurality of tubular bodies adapted to be mounted in side-by-side relation on a motorized highway vehicle in mutual parallelism with the axis of a path of travel for said vehicle, each body of said plurality of bodies being formed from a length of cylindrical tubing and having,
        i. a first opening and a second opening, said openings being defined at the opposite ends of said body,
        ii. a first and a second sealing cap, each cap being pivotally mounted on the body, said first cap being characterized by a first pivotal plate mounted adjacent said first opening having an arm angularly projected therefrom, and a first plug releasably mounted on one face of the first plate tapered to be received in hermetically sealed relation within said first opening and sized to pass axially through the body while maintaining a sealed engagement with the internal surface of the body, said second cap being characterized by a second pivotal plate having an arm projected therefrom, and a second plug affixed to one face of said second plate and tapered to be received in hermetically sealed relation with said second opening,
        iii. a mandrel affixed to the first plug and projected through the first plate, and a nipple affixed to the second plug and extended through said second plate adapted to receive a gas-extraction tube in communicating relation with the interior of said body,
        iv. a pair of torsion springs, each being connected to one of said caps, independently of the other, for urging said caps in pivotal displacement toward adjacent openings defined in the ends of said body,
        v. releasable restraint means for securing said caps against pivotal displacement including a tensioned line having its opposite ends connected to the arms projected from the first and second plates,
        vi. release means including a remotely controlled, electrically energizable hot wire cutter mounted adjacent the mid-portion of said line for severing the line, and
        vii. a push-rod adapted to be connected to said mandrel in axial alignment therewith for accommodating application of an axial force to said first plug for causing said first plug to separate from said plate and axially pass through said body for discharging entrapped quantities of gas through said nipple.

5. Apparatus for capturing a tracer sample of atmospheric gasses comprising:
- a container having an opening at each of its opposite ends:
  - a push rod and a tubular conduit;
  - a pair of pivotal, spring-biased plates, each plate supporting a sealing plug, one plug having affixed thereto means for attaching said tubular conduit in communicating relation with the interior of said container, and the other plug having affixed thereto means for attaching said push rod to the plug through its supporting plate,
  - releasable restraint means for holding each of said plates away from openings at both ends of said cylindrical container against the spring bias thereof;
- means for establishing a stream of atmospheric gasses through said container while open at both ends; and
- means for releasing said restraint means to allow said plates to simultaneously close the opening at each end of said container with said plugs;
- whereby, upon releasing said restraint means, a sample of terrestial atmospheric gasses is trapped in said container, and by pushing said rod the sample may be extracted from said container.

* * * * *